(12) United States Patent
Mate et al.

(10) Patent No.: US 7,657,302 B2
(45) Date of Patent: *Feb. 2, 2010

(54) GUIDED RADIATION THERAPY SYSTEM

(75) Inventors: Timothy P. Mate, Bellevue, WA (US); Steven C. Dimmer, Bellevue, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 94 days.

This patent is subject to a terminal disclaimer.

(21) Appl. No.: 10/722,015

(22) Filed: Nov. 25, 2003

(65) Prior Publication Data

US 2005/0261570 A1    Nov. 24, 2005

Related U.S. Application Data

(63) Continuation of application No. 09/877,498, filed on Jun. 8, 2001.

(51) Int. Cl.
    *A61B 5/05*      (2006.01)
    *A61B 19/00*     (2006.01)
    *A61N 5/10*      (2006.01)

(52) U.S. Cl. .................... 600/424; 378/65; 128/899

(58) Field of Classification Search ................. 600/427, 600/411, 436; 378/65, 205; 128/899
    See application file for complete search history.

(56) References Cited

U.S. PATENT DOCUMENTS 4,017,858 A    4/1977    Kuipers
4,466,075 A    8/1984    Groch
4,642,786 A    2/1987    Hansen
4,737,794 A    4/1988    Jones (Continued)

FOREIGN PATENT DOCUMENTS

EP    0 719 420    11/1999

(Continued)

OTHER PUBLICATIONS

International Preliminary Examination Report; PCT/US02/17876, filed Jun. 5, 2002, in the name of Calypso Medical Technologies, Inc.

(Continued)

*Primary Examiner*—Eric F Winakur
*Assistant Examiner*—Michael T Rozanski
(74) *Attorney, Agent, or Firm*—Perkins Coie LLP

(57) ABSTRACT

A system and method for accurately locating and tracking the position of a target, such as a tumor or the like, within a body. In one embodiment, the system is a target locating and monitoring system usable with a radiation delivery source that delivers selected doses of radiation to a target in a body. The system includes one or more excitable markers positionable in or near the target, an external excitation source that remotely excites the markers to produce an identifiable signal, and a plurality of sensors spaced apart in a known geometry relative to each other. A computer is coupled to the sensors and configured to use the marker measurements to identify a target isocenter within the target. The computer compares the position of the target isocenter with the location of the machine isocenter. The computer also controls movement of the patient and a patient support device so the target isocenter is coincident with the machine isocenter before and during radiation therapy.

10 Claims, 10 Drawing Sheets

U.S. PATENT DOCUMENTS

| | | |
|---|---|---|
| 4,849,692 A | 7/1989 | Blood |
| 4,945,305 A | 7/1990 | Blood |
| 5,050,608 A | 9/1991 | Watanabe |
| 5,099,845 A | 3/1992 | Besz |
| 5,188,368 A | 2/1993 | Ryan |
| 5,198,877 A | 3/1993 | Schulz |
| 5,221,269 A | 6/1993 | Miller |
| 5,240,011 A | 8/1993 | Assa |
| 5,325,873 A | 7/1994 | Hirschi |
| 5,377,678 A | 1/1995 | Dumoulin |
| 5,397,329 A | 3/1995 | Allen |
| 5,411,026 A | 5/1995 | Carol |
| 5,417,210 A | 5/1995 | Funda |
| 5,425,382 A | 6/1995 | Golden |
| 5,446,548 A | 8/1995 | Gerig |
| 5,453,686 A | 9/1995 | Anderson |
| 5,515,853 A | 5/1996 | Smith |
| 5,526,812 A | 6/1996 | Dumoulin |
| 5,528,651 A | 6/1996 | Leksell |
| 5,546,951 A | 8/1996 | Ben-Haim |
| 5,558,091 A | 9/1996 | Acker |
| 5,568,809 A | 10/1996 | Ben-Haim |
| 5,572,999 A | 11/1996 | Funda |
| 5,617,857 A | 4/1997 | Chader |
| 5,622,170 A | 4/1997 | Schulz |
| 5,622,187 A | 4/1997 | Carol |
| 5,629,967 A | 5/1997 | Leksell |
| 5,630,431 A | 5/1997 | Taylor |
| 5,681,326 A | 10/1997 | Lax |
| 5,727,552 A | 3/1998 | Ryan |
| 5,745,545 A | 4/1998 | Hughes |
| RE35,816 E | 6/1998 | Schulz |
| 5,779,638 A | 7/1998 | Vesely |
| 5,797,849 A | 8/1998 | Vesely |
| 5,805,661 A | 9/1998 | Leksell |
| 5,817,022 A | 10/1998 | Vesely |
| 5,820,553 A | 10/1998 | Hughes |
| 5,823,192 A | 10/1998 | Kalend |
| 5,828,770 A | 10/1998 | Leis |
| 5,830,144 A | 11/1998 | Vesely |
| 5,868,673 A | 2/1999 | Vesely |
| 5,868,675 A | 2/1999 | Henrion |
| 5,879,357 A | 3/1999 | Heaton |
| 5,902,238 A | 5/1999 | Golden |
| 5,902,310 A | 5/1999 | Foerster |
| 5,913,820 A | 6/1999 | Bladen |
| 5,923,417 A | 7/1999 | Leis |
| 5,987,349 A | 11/1999 | Schulz |
| 6,015,390 A | 1/2000 | Krag |
| 6,019,725 A | 2/2000 | Vesely |
| 6,026,818 A | 2/2000 | Blair |
| 6,049,587 A | 4/2000 | Leksell |
| 6,052,477 A | 4/2000 | Wang |
| 6,061,644 A | 5/2000 | Leis |
| 6,064,904 A | 5/2000 | Yanof |
| 6,067,465 A | 5/2000 | Foo |
| 6,094,007 A | 7/2000 | Faul |
| 6,097,994 A | 8/2000 | Navab |
| 6,144,875 A | 11/2000 | Schweikard |
| 6,173,715 B1 | 1/2001 | Sinanan |
| 6,239,724 B1 * | 5/2001 | Doron et al. ............ 340/870.28 |
| 6,307,473 B1 | 10/2001 | Zampini et al. |
| 6,363,940 B1 | 4/2002 | Krag |
| 6,401,722 B1 | 6/2002 | Krag |
| 6,405,072 B1 * | 6/2002 | Cosman ..................... 600/426 |
| 6,474,341 B1 | 11/2002 | Hunter |
| 6,611,700 B1 * | 8/2003 | Vilsmeier et al. ........... 600/407 |
| 2005/0059884 A1 | 3/2005 | Krag |
| 2006/0079764 A1 * | 4/2006 | Wright et al. ............... 600/431 |

FOREIGN PATENT DOCUMENTS

| | | |
|---|---|---|
| EP | 1 034 738 | 9/2000 |
| WO | WO-88/08282 | 11/1988 |
| WO | WO-95/33519 | 12/1995 |
| WO | WO-96/08208 | 3/1996 |
| WO | WO-96/08999 | 3/1996 |
| WO | WO-97/36192 | 10/1997 |
| WO | WO-97/48438 | 12/1997 |
| WO | WO-99/17133 | 4/1999 |
| WO | WO-99/27839 | 6/1999 |
| WO | WO-99/30182 | 6/1999 |
| WO | WO-99/35966 | 7/1999 |
| WO | WO-99/58055 | 11/1999 |
| WO | WO-00/24332 | 5/2000 |
| WO | WO-00/51514 | 9/2000 |
| WO | WO-01/34049 | 5/2001 |
| WO | WO-01/54765 | 8/2001 |
| WO | WO-02/19908 | 3/2002 |
| WO | WO-02/100485 | 12/2002 |

OTHER PUBLICATIONS

Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science.

International Search Report dated Jan. 24, 2003, PCT Application No. PCT/US/29390.

Final Office Action; U.S. Appl. No. 09/877,498; Applicant: Calypso Medical Technologies, Inc.; Date of Mailing: Feb. 14, 2006; 7 pages.

Decision on Appeal, U.S. Appl. No. 09/877,498, Applicant: Calypso Medical Technologies, Inc., Date of Mailing: May 27, 2009, 16 pages.

Non-Final Office Action; U.S. Appl. No. 09/877,498; Mailed Aug. 7, 2009 (6 pgs.).

* cited by examiner

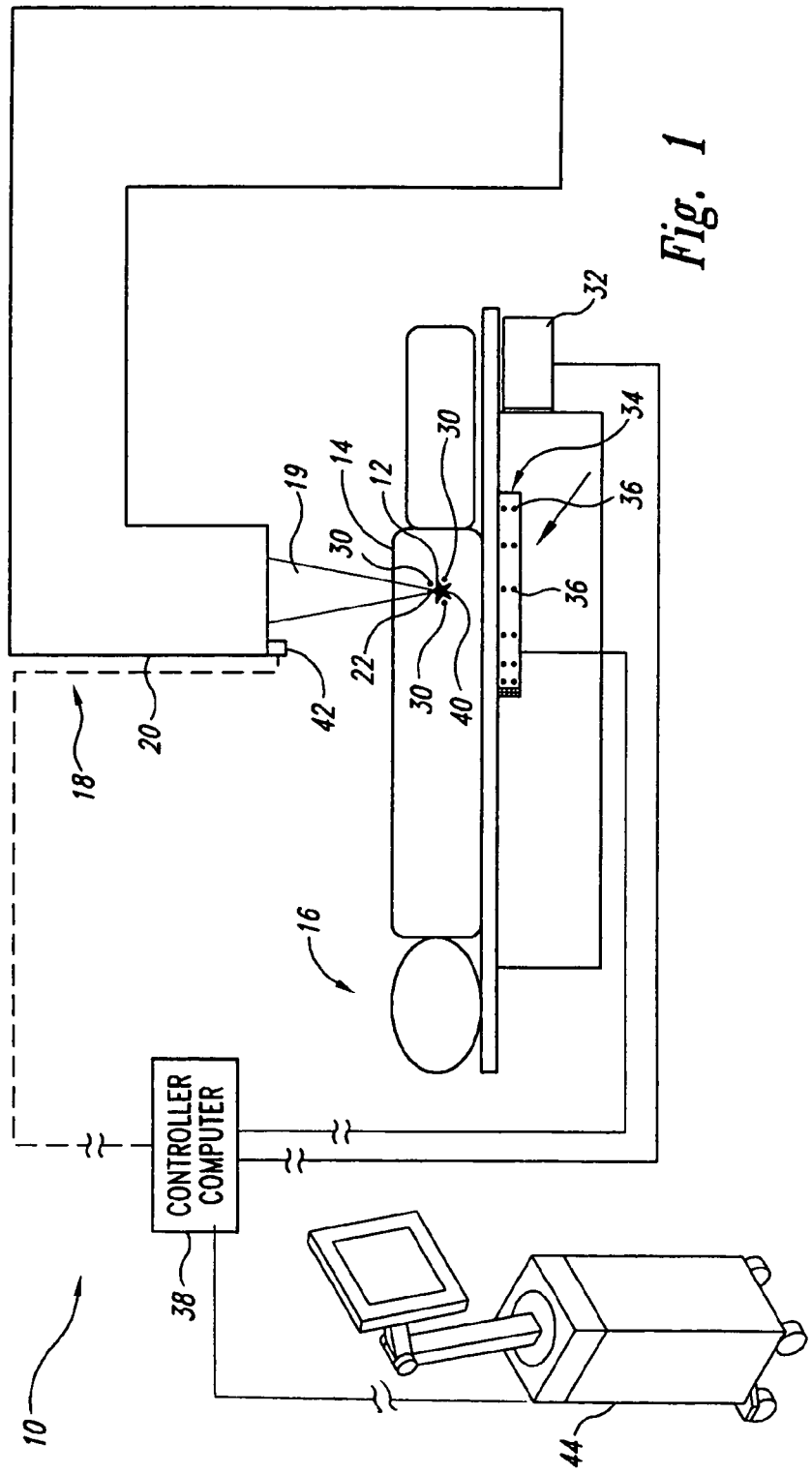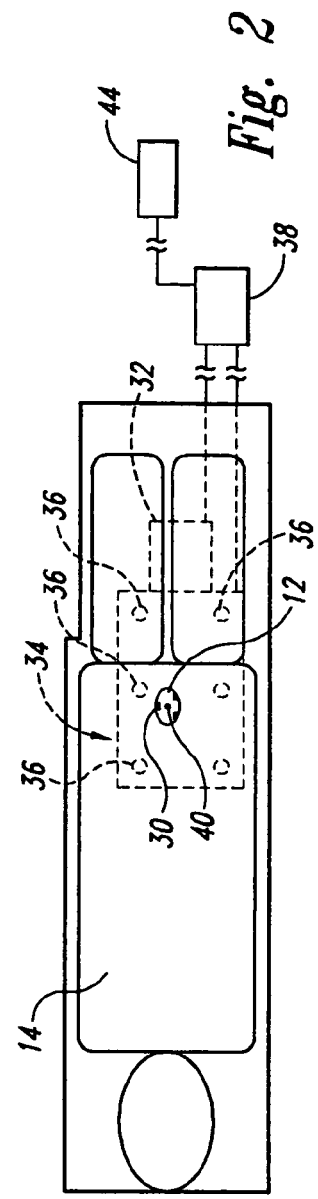

GUIDED RADIATION THERAPY SYSTEM

CROSS-REFERENCE TO RELATED APPLICATION(S)

This application is a continuation of Ser. No. 09/877,498 filed Jun. 8, 2001, and is related to co-pending application Ser. No. 10/721,491, titled GUIDED RADIATION THERAPY SYSTEM, filed Nov. 24, 2003, both of which are hereby incorporated by reference.

TECHNICAL FIELD

This invention relates generally to radiation therapy systems, and more particularly to systems and methods for accurately locating and tracking a target in a body to which guided radiation therapy is delivered.

BACKGROUND OF THE INVENTION

Recent advances in radiation therapy are providing new avenues of effective treatment for localized cancer. These include three-dimensional conformal external beam radiation, intensity modulated radiation therapy (IMRT), and stereotactic radiosurgery and brachytherapy. These newer treatment modalities deliver greater doses of radiation to the tumor, which accounts for their increased effectiveness when compared to standard external beam radiation therapy.

To achieve continued improvements in the management of localized cancers with radiotherapy, further dose escalation is necessary because a dose response relationship for radiotherapy exists for most cancers. However, with the increased dose of delivered radiation comes the potential for increased complications to healthy tissues, unless measures are taken to reduce the amount of adjacent normal tissue irradiated. Effective radiation treatments are dependent upon both total dose of radiation and the volume of normal tissue irradiated around the tumor. Therefore, as the radiation dose is increased, the volume of adjacent normal tissue irradiated must be decreased in order to keep an equivalent rate of effective radiation treatment.

To reduce the amount of adjacent normal tissue that is irradiated, one must prescribe the radiation to the target with a tighter treatment margin, that being an area of healthy tissue around the target that receives the full dose of prescribed radiation. For example, if the treatment margin for prostate cancer is too large, the margin may encompass some rectal, bladder and bulbar urethral tissues. It is highly desirable to provide a margin that does not encompass these important tissues.

It would be ideal to have no treatment margin at all. Some margin has been necessary, however due to day-by-day variability in the initial radiation treatment setup and delivery with existing systems. Margins have also been needed to accommodate for potential internal movement of a target within the patient's body that can occur even when the exterior portion of the patient remains stationary. Several studies have documented and quantified that tumor motion in the prostate occurs during radiation treatment, primarily due to the patient's breathing, and due to natural rectal and bladder filling and emptying. Without some treatment margin, the potential exists that the tumor itself could move out of the treatment volume.

In addition, if the patient is set up so the radiation beam is initially off target, or if the target moves during treatment, the beam hits more of the normal tissue and causes increased collateral damage to the normal tissue, as well as potentially under-dosing the target. It is highly desirable to prevent as much collateral damage to normal tissue as possible. Thus, day-by-day, minute-by-minute changes in radiation treatment setup and target motion have posed serious challenges when dose escalation is attempted with current patient setup processes.

Current patient setup procedures are reliant upon alignment of external reference markings on the patient's body with visual alignment guides for the radiation delivery device. As an example, a tumor is identified within a patient's body with an imaging system, such as an X-ray, computerized tomography (CT), magnetic resonance imaging (MRI), or ultrasound system. The approximate location of a tumor in the body is aligned with two or more alignment points on the exterior of the patient's body, and external marks are written on the patient's skin to mark the alignment points.

During the patient setup for radiation treatment, the external marks are aligned with a reference system of the radiation delivery devices. This setup process attempts to accurately position the treatment target (or patient) isocenter within the body at a position in space where the radiation beam is focused, known as the machine isocenter. By precisely positioning the treatment target with respect to the machine isocenter, the effective patient treatment volume within the body is accurately registered (or positioned) to the radiation therapy treatment plan location. If, however, the target has moved relative to the external marks, then the target may be offset from the machine's isocenter, even when the external aligning devices and marks are properly aligned. Accordingly, the doctors and technicians cannot tell how far the target has actually moved relative to the machine's isocenter. As an example, studies have documented target displacements of up to 1.6 cm between two consecutive days of prostate radiotherapy treatment. Substantial target displacement of lung tumors in a very short time period has also been documented because of the patient's breathing and heartbeats. Such internal motion of the target can cause inaccuracies in treatment deliveries, so larger margins of healthy tissue are prescribed and irradiated to compensate for likely internal target motions.

SUMMARY OF THE INVENTION

Under one aspect of the invention, a system and methods are provided for accurately locating and tracking the actual position of a target within a body in preparation for and during radiation therapy. In one embodiment, the system is usable with a radiation delivery source that delivers a selected dose of radiation to the target in the body when the target is positioned at the machine isocenter of the radiation delivery source. The system includes a marker fixable in or on the body at a selected position relative to the target, such as in or near the target. The marker is excitable by an external excitation source to produce an identifiable signal while affixed in or on the body. A sensor array with a plurality of sensors is provided external of the body, and the sensors are spaced apart in a known geometry relative to each other.

A data-processing unit is coupled to the sensor array and is configured to use the measurements from the sensors to determine the actual location of the marker and a target isocenter within the target relative to the sensors. A reference marker is also coupled to the radiation delivery device at a known position relative to the device's machine isocenter. The reference marker provides a measurable signal for determining the position of the reference marker and the machine isocenter relative to the sensor array. The data-processing unit is configured to compare the position of the target isocenter with the position of the machine isocenter in real time to determine whether the patient is properly setup for the radiation therapy.

Under another aspect of the invention, a monitoring system is coupled to the data-processing unit and has a feedback portion configured to provide feedback information about the actual position of the target isocenter relative to the machine isocenter. In one embodiment, the feedback portion provides a visual and/or numeric representation of the positions of the machine isocenter and target isocenter relative to each other. This representation may then be used to adjust the position of the target isocenter before or during therapy. In another embodiment, the feedback portion provides a visual and/or numeric display of the real-time movement of the target isocenter relative to the machine isocenter. Additionally, the feedback data may be used to automatically alert the operator of patient or target movement beyond acceptable limits. In a third embodiment, the feedback data may be used to automatically adjust, gate or shutoff the radiation therapy treatment for normal (i.e. respiration) or unplanned patient motion.

Under another aspect of the invention, an adjustable patient support assembly is combined with the tracking and monitoring system for use with the radiation delivery system. The support assembly includes a base, a support structure movably attached to the base, and a movement control device connected to the support structure in order to selectively move the support structure relative to the base. The plurality of sensors spaced apart from each other are coupled to the base in a fixed location relative to the base. The data-processing unit is coupled to the sensors to receive the signal measurement data from one or more markers in or next to the target. The data-processing unit is configured to use the signal measurement data for each marker to determine the actual location of the marker and target isocenter within the target. The data-processing unit is configured to identify the location of the target isocenter relative to the machine isocenter. The movement control device is coupled to the data-processing unit and is adapted to position the target isocenter coincident with the machine isocenter in response to data from the data processing unit.

Under another aspect of the invention, a method is provided for delivering radiation therapy on a selected target within a body. The method includes positioning an excitable marker at a selected position relative to the target, exciting the implanted marker with an excitation source external of the body to produce an identifiable marker signal and measuring the marker signal from the marker with a plurality of sensors exterior of the body, positioned in a known geometry relative to each other. The method also includes determining the location of the marker and a target isocenter in the body relative to the sensors based upon the measurements of the marker signal from the sensors. The method further includes determining the location of a machine isocenter of the radiation delivery assembly relative to the sensors and relative to the target isocenter, and positioning the body relative to the radiation delivery device so the target isocenter is coincident with the machine isocenter. Radiation therapy is then applied from the radiation delivery device to the treatment volume about the target isocenter.

In yet another aspect of the invention, a method is provided for positioning a body relative to a radiation delivery device for delivering radiation therapy to a treatment volume at a target isocenter within the body. The body has a selected target therein, and at least one excitable marker is positioned in a known position relative to the target. The method includes positioning the body on a movable support assembly adjacent to a plurality of sensors, and energizing the excitable marker with an excitation source exterior of the body. The excited marker provides an identifiable marker signal. The marker signal is measured with the plurality of sensors positioned exterior of the body and in a known geometry relative to each other and relative to the movable support assembly. The location of the marker and a target isocenter within the treatment volume is determined based on the measurements by the sensors of the marker signal. The location of the target isocenter is also determined relative to the plurality of sensors and relative to the machine isocenter. The location of the target isocenter is compared to the location of the machine isocenter, and if the two isocenters are not coincident with each other, a portion of the support assembly moves the body and target to position the target isocenter coincident with the machine isocenter.

BRIEF DESCRIPTION OF DRAWINGS

FIG. 1 is a schematic side elevation view of a target locating and monitoring system in accordance with an embodiment of the present invention. Excitable markers are shown implanted in or adjacent to a target in a patient's body, a sensor array is shown exterior of the patient, and a radiation delivery device is shown in a position to apply radiation therapy to the target within the body.

FIG. 2 is a schematic top plan view of the patient on a movable support table, with the implanted markers, the target, and the sensor array shown in hidden lines.

DETAILED DESCRIPTION

Figure 3:
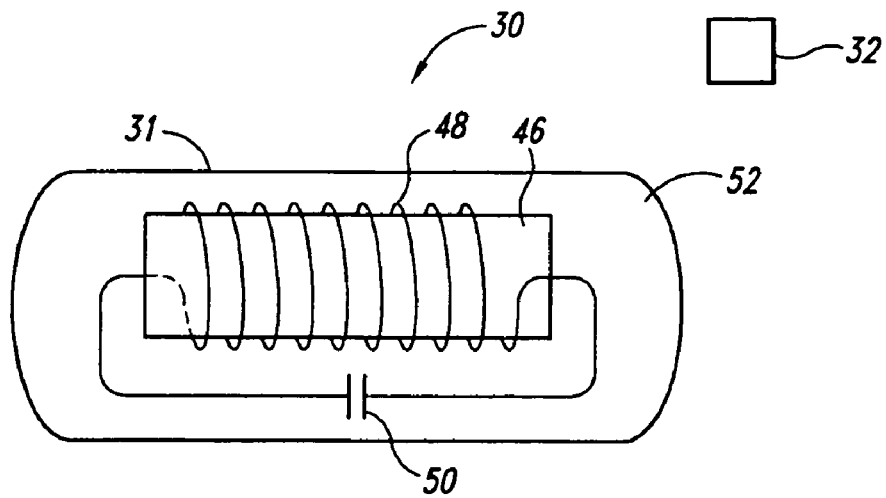
FIG. 3 is an enlarged side elevation view of one embodiment of a single-axis marker usable in the system illustrated in FIG. 1.

FIGS. 1-17 illustrate a system and several components for locating, tracking and monitoring a target within a body in accordance with embodiments of the present invention. The system and components are usable to locate, track, monitor, and evaluate a target for application of a selected therapy to the target, such as guided radiation therapy. Several of the components described below with reference to FIGS. 1-17 can also be used in systems for performing methods in accordance with aspects of the present invention. Therefore, like reference numbers refer to like components and features throughout the various figures.

Referring to FIGS. 1 and 2, one aspect of the present invention provides a system 10 configured for use in applying guided radiation therapy to a target 12, such as a tumor, within the body 14 of a patient 16. The system 10 allows the target 12 to be located within the patient's body 14 and the actual position monitored in real time while applying ionizing radiation therapy to the target from a radiation delivery source 18. The target 12 may move within the body 14 because of breathing, organ filling or emptying, or other internal movement. The target motion is tracked and monitored relative to the radiation beam to insure accurate delivery of radiation to the target 12 and, if needed, only a minimum margin around the target. While the system 10 is discussed below in connection with guided radiation therapy for radiation of a tumor or other target, the system can be used for tracking and monitoring other targets within a body, such as for other therapeutic or diagnostic purposes.

The radiation delivery source 18 of the illustrated embodiment (FIG. 1) is an ionizing radiation device, known as a linear accelerator, but could be any radiation therapy delivery device. Other radiation therapy delivery devices can be used, including such devices manufactured by Varian Medical Systems, Inc. of Palo Alto, Calif.; Siemans Medical Systems, Inc. of Iselin, N.J.; Electa Instruments, Inc. of Iselin, N.J.; or Mitsubishi Denki Kabushik Kaisha of Japan. Such devices are used to deliver conventional single or multi-field radiation therapy, 3D conformal radiation therapy (3D CRT), inverse modulated radiation therapy (IMRT), stereotactic radiotherapy, and tomo therapy. This is done in conjunction with a variety of treatment planning software systems.

The radiation delivery source 18 delivers a gated, contoured or shaped beam 19 of ionizing radiation from a movable gantry 20 to a area or volume referenced to a point at a location away from the gantry. This point in space, referred to as a machine isocenter 22, is the point to which the ionizing radiation beam 19 is configured about as determined by industry standard treatment planning processes. The system 10 allows the target 12 to be accurately positioned at the machine isocenter 22 so the ionizing radiation is accurately delivered to the target 12. The system also allows the target's actual position relative to the machine isocenter 22 to be monitored during the radiation therapy so as to minimize collateral damage to healthy tissue surrounding the target.

The illustrated system 10 includes a plurality of markers 30 positioned in or adjacent to the target 12 to mark the target's actual location in the body 14. Accordingly, the markers 30 are markers in, on or near the body. In one example, the markers 30 may be attached to patient-immobilization devices at known locations relative to the treatment isocenter. The markers 30 are energized or excited by an excitation source 32 positioned exterior of the patient's body 14. When the markers 30 are excited, they each resonate at a selected unique frequency and generate a low energy radio-frequency magnetic signal measurable from outside of the body 14. The signals from the markers 30 are detected and measured by an array 34 of sensors 36 located exterior of the patient's body 14. The sensors 36 are positioned in a fixed, selected geometry relative to each other, so the array 34 defines a fixed reference coordinate system from which location and movement are calculated. The sensors 36 are operatively coupled to a computer controller 38 that receives the measurement information from each sensor and determines the actual location of the markers 30 within the patient's body 14 relative to the sensors.

In one embodiment, the computer controller 38 includes algorithms used to define and determine the location of the target isocenter 40 within the target 12, based upon the signal measurements by the sensors 36 from the resonating markers. In another embodiment, the location of the target isocenter 40 within the target 12 is selected, and the computer controller 38 utilizes position information about the position and/or orientation of each marker 30 relative to the selected target isocenter. The target isocenter 40 is the point or position within the target to which the shaped dose of radiation is configured around or referenced to as determined by a treatment planning process. In one embodiment, the sensors 36 are polled twelve or more times per minute to track the actual position of the target isocenter 40 within the patient's body 14 relative to the sensor array 34. Accordingly, the actual position of the target 12 and the target isocenter 40 can be monitored in real time when the patient is positioned adjacent to the sensor array 34.

The actual position of the target isocenter 40 is compared to the position of the machine isocenter 22 relative to the sensor array 34. The illustrated system 10 has a reference device 42 positioned on the gantry 20 of the linear actuator or another selected position on a radiation therapy delivery device used in alternate embodiments. In these alternate embodiments, the other radiation therapy delivery device can include cobalt machines, a Gamma Knife, a Cyberknife, specialized stereostatic radiotherapy devices, or a TomoCT assembly (which utilizes a linear actuator in a CT scanner). The reference device 42 is positioned at a known spatial or geometric relationship relative to the machine isocenter 22. The reference device 42 in one embodiment is a resonating, three axis, single frequency marker that provides a measurable signal detectable by the sensors 36 in the array 34. The reference device 42 in alternate embodiments can be positioned in a remote location away from the gantry 20. In either embodiment, the location of the machine isocenter 22 relative to the sensor array 34 can be calculated upon determining the position of the reference device 42 relative to the sensor array. The sensors 36 provide the measurement data about the reference device 42 to the computer controller 38, and the computer controller calculates the location of the machine isocenter 22 relative to the sensor array 34.

The location of the target isocenter 40 relative to the sensor array 34 is compared to the position of the machine isocenter 22 relative to the sensor array. If the target isocenter 40 and machine isocenter 22 are spatially misaligned such that the two isocenters are not three-dimensionally coincident with each other, the patient 16, and/or target 12 can be moved relative to the machine isocenter 22. The target 12 position is moved until the target isocenter 40 is coincident with the machine isocenter 22. Once the target and machine isocenters 40 and 22 are acceptably aligned, the radiation delivery source 18 can be activated to provide the ionizing radiation beam 19 referenced to the target isocenter, thereby irradiating the target according to a radiation treatment plan, while minimizing or eliminating collateral damage to healthy tissue surrounding the target 12. The actual location of the target isocenter 40 can also be monitored in real time during the radiation therapy to ensure that the target isocenter does not move an unacceptable amount relative to the machine isocenter 22 and allow for treatment when the treatment isocenter and the machine isocenter are within acceptable displacement limits.

In the illustrated embodiment, the system 10 also includes a monitoring assembly 44 coupled to the computer controller 38 that provides feedback data to a user interface for the doctor or technician operating the system and/or the radiation delivery device 18. As an example, the monitoring assembly 44 can provide the feedback data as a visual representation of the target isocenter's position in three-dimensional space relative to the machine isocenter's position in real time as the patient is being set up and positioned for the radiation therapy. The monitoring assembly 44 can also provide other feedback data to the user interface including, for example, confirmation of setup completion, graphical information, patient information, radiation treatment plan information, or other information that can be utilized during the guided radiation therapy process.

Figure 4:
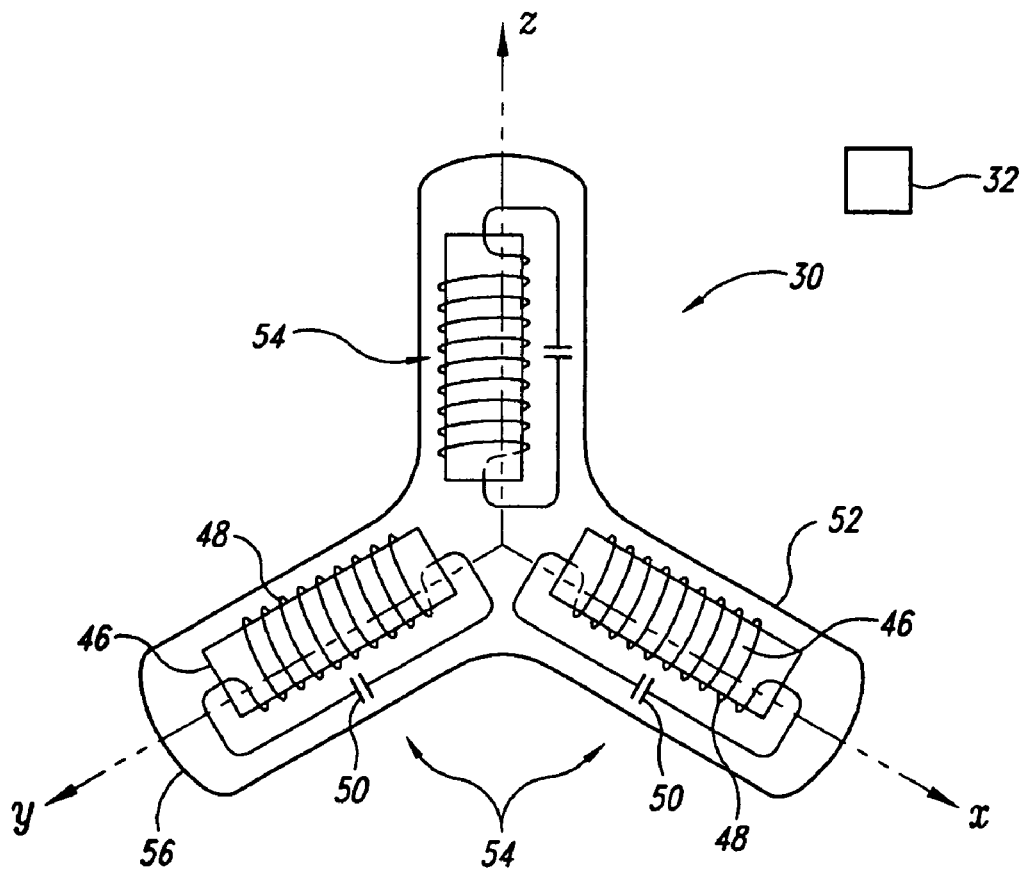
FIG. 4 is an enlarged side elevation view of one embodiment of a three-axis marker usable in the system of FIG. 1.
Figure 5:
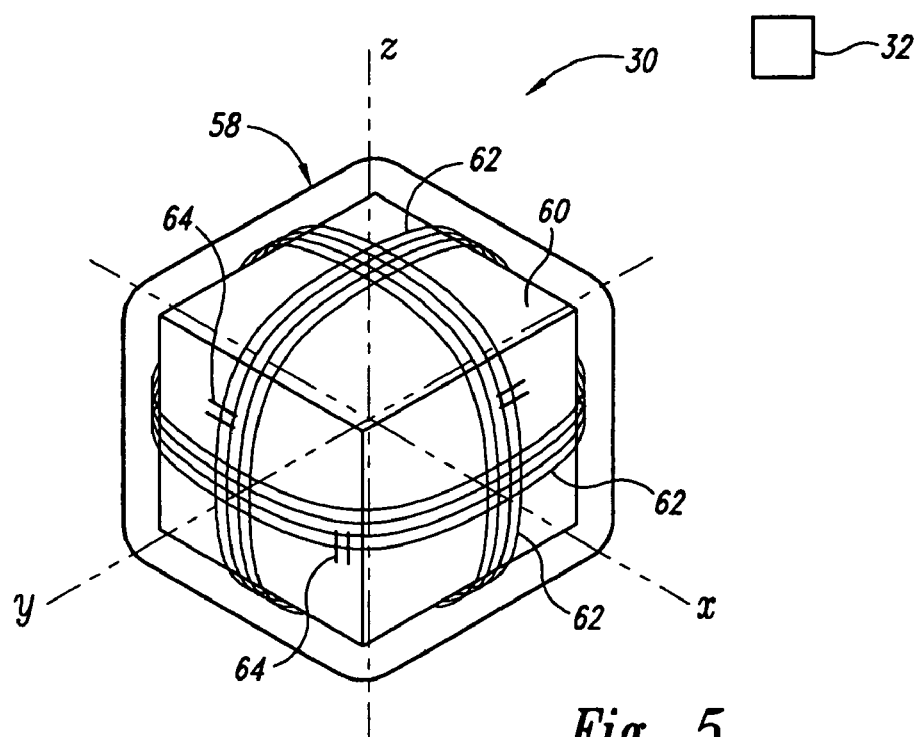
FIG. 5 is an enlarged isometric view of another embodiment of a three-axis marker usable in the system of FIG. 1.

FIGS. 3-5 illustrate excitable markers 30 of alternate embodiments usable in the system 10. One of the markers 30 shown in FIG. 3 is an implantable, single-axis, resonating marker 31 having a ferrite core 46 wrapped by a conductive winding 48, and the winding is connected to a small capacitor 50. The marker 31 is configured to be energized by the external excitation source 32, which produces an electromagnetic field. This electromagnetic field causes the marker 31 to resonate at a predetermined frequency, thereby providing a signal of sufficient intensity to be measured by the sensors 36 (FIG. 1) from outside of the body. A biologically inert coating 52 encapsulates the ferrite core 46, the winding 48, and the capacitor 50 so as to provide a small, self-contained, wireless excitable marker 31 that can be permanently implanted into the patient. In this embodiment, the marker 31 is "wireless" because it need not be physically connected via wires to an outside energy source for generation or communication of the marker signal. In one embodiment, the marker 31 has a length of only approximately 5 mm and diameter sized to fit through an applicator needle. The marker 31 in other embodiments can have different sizes as needed for the desired configuration of the marker signal.

As best seen in FIG. 4, another one of the excitable markers 30 includes a three-axis, wireless, resonating marker 52 with three signaling portions 54. Each signaling portion 54 is positioned axially perpendicular to the other two signaling portions. Accordingly, the three signaling portions 54 define an X, Y, Z reference coordinate. Each of the signaling portions 54 includes a ferrite core 46, a winding 48 around the ferrite core, and a small capacitor 50 connected to each winding. Each signaling portion is configured to be energized by the external excitation source 32, and to resonate at a frequency different than the resonating frequency of the other two signaling portions.

In one embodiment, as illustrated in FIG. 4, the three-axis marker 52 includes a biologically inert coating 56 that encapsulates all three of the signaling portions 54, so the marker can be permanently implanted in the patient's body. When the marker 52 is energized by the external excitation source 32, each of the marker's signaling portions resonates at its selected frequency and provides the measurable marker signal at an intensity so it can each be measured by the sensor array 34 (FIG. 1). Frequency multiplexing by the computer controller allows the computer controller 38 to differentiate between the marker signals from the different signaling portions of the marker when calculating the marker's position and orientation relative to the sensor array.

As best seen in FIG. 5, another embodiment of the marker 30 includes a cube-shaped marker 58 with a single ferrite core 60 and three sets of windings 62 axially oriented perpendicular to each other to define the X, Y, and Z axes for the marker. Each winding 62 is connected to a small capacitor 64 and configured to resonate at a frequency different than the other two windings. Accordingly, the cube-shaped marker 58 is also a wireless, three-axis, resonating marker.

In one embodiment, the wireless, excitable markers 30 are configured to resonate and provide a measurable signal within the frequency range of approximately 10 kHz to 200 kHz, inclusive. In other embodiments, the markers 30 can be self-contained, powered markers that include a power source, such as a battery, that provides sufficient power to produce the measurable identifiable marker signal. In other embodiments, the markers 30 can be "wired" markers connectable via wires to a selected power or excitation source to allow the markers to generate the unique marker signal. The marker signal can be unique as a function of frequency (i.e., frequency multiplexing) as a function of time or time multiplexing.

In selected applications, a single marker 31, preferably a single-axis marker, is implanted in the target 12, and the intensity of the signals from the single resonating marker is used to determine the target location information relative to the sensor array 34. In alternate embodiments, two, three, or more markers 30 are implanted at known locations in or adjacent to the target. Each marker 30 produces its unique signal relative to the other markers, so the sensor array 34 differentiates between the markers by frequency multiplexing. The sensor array 34 measures the intensity of the unique signals from the markers 30. The signal intensity measurements are converted for use in geometric calculations (discussed in greater detail below) to accurately determine the actual three-dimensional location (X, Y, Z) and possibly the angular orientation (pitch, yaw, roll) of the marker relative to the sensor array 34.

Referring again to FIG. 1, the system 10 includes the excitation source 32 that generates a magnetic field for exciting the markers 30. The excitation source is positioned in a selected location relative to the target 12 and close enough to the markers 30 so the emitted magnetic field has sufficient intensity to acceptably energize the markers. In the illustrated embodiment, a plurality of markers 30 are permanently implanted within the patient's body 14 in or adjacent to the target 12. In one embodiment, the computer controller 38 provides a separate driver circuit for the excitation source 32 for each marker 30, so as to selectively excite the respective marker at the selected frequency. The excitation source 32 in one embodiment is a three-dimensional, AC magnetic field source that generates three-dimensional magnetic fields in the X, Y, and Z axes. This excitation source 32 provides one source coil for each marker 30, and the electric current driven through the source coil generates the AC magnetic waveform tuned for the respective markers. In another embodiment, the source coil (or coils) in the excitation source 32 is provided by a coil configured to generate the multiple or scanned excitation frequency fields for the respective markers 30.

Figure 6:
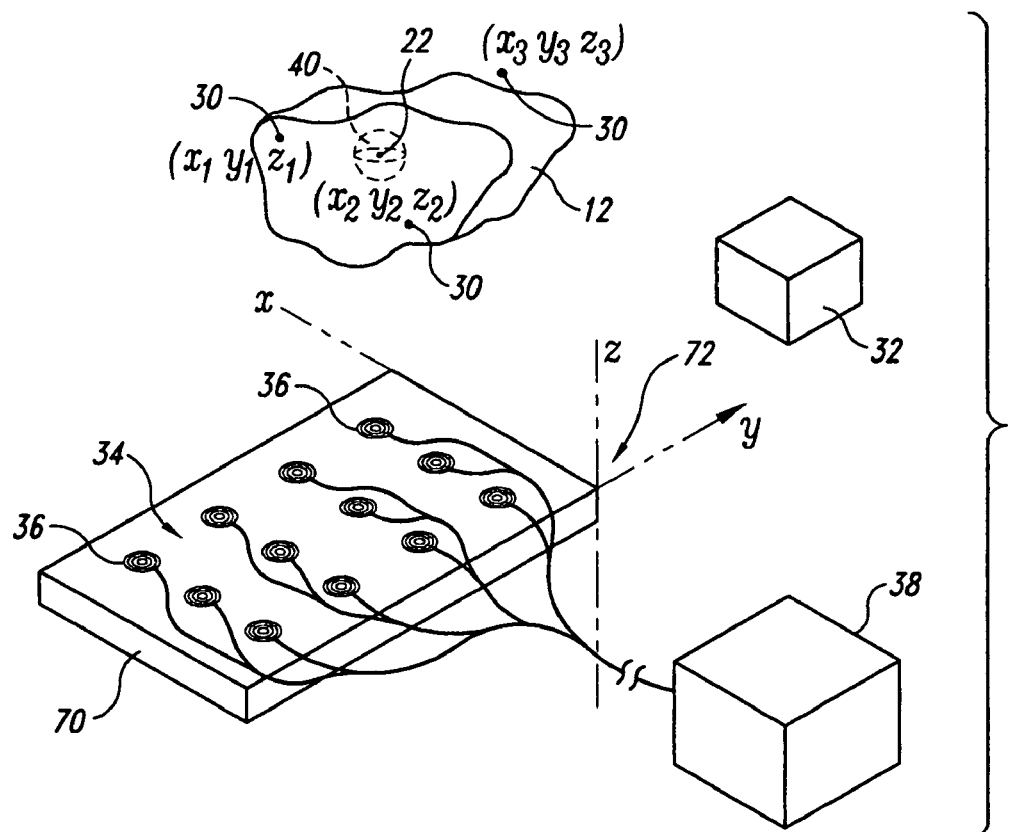
FIG. 6 is an enlarged partial schematic isometric view of the target, three markers implanted in or near the target, an external excitation source, the sensor array, and a computer controller in the system of FIG. 1.
Figure 7:
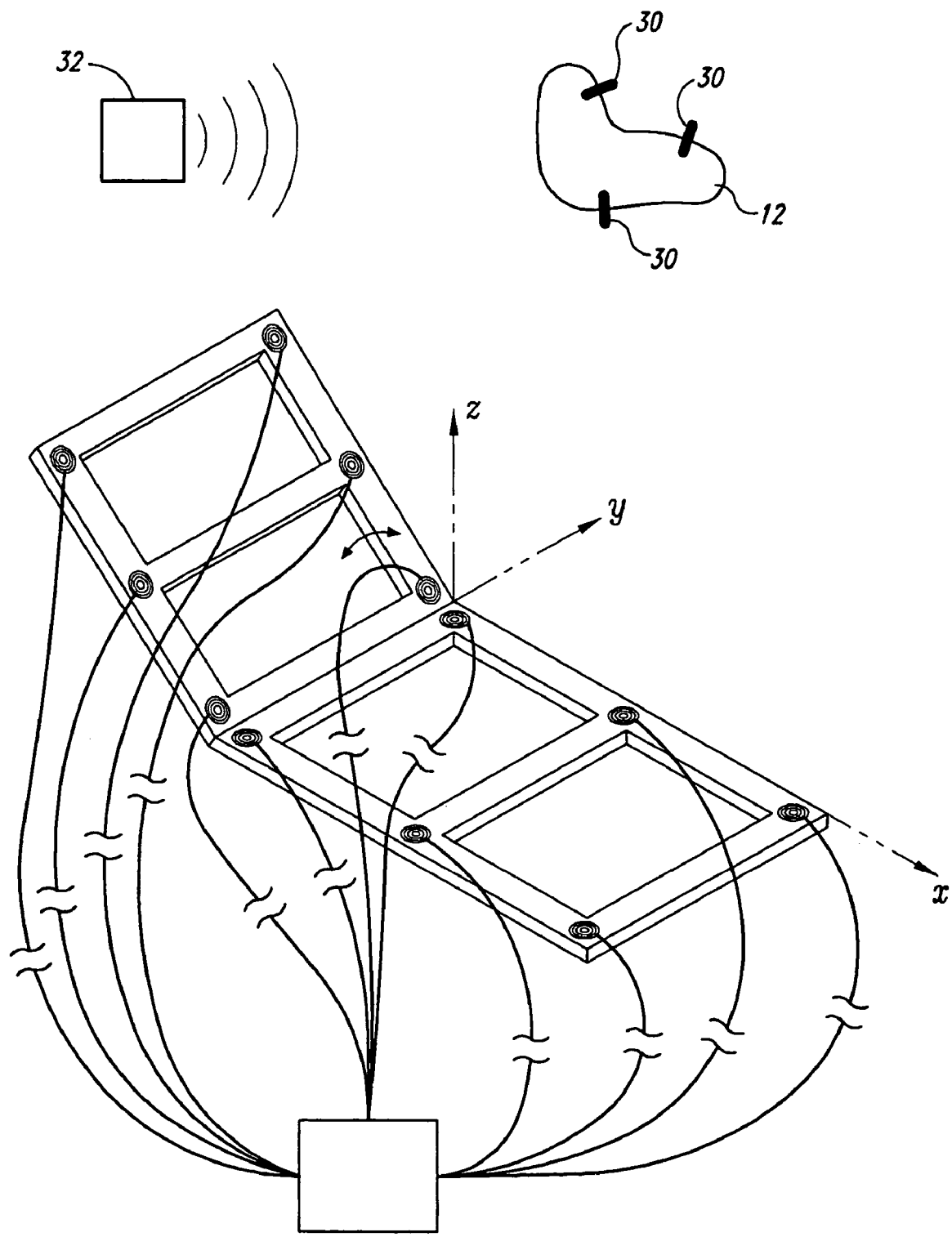
FIG. 7 is a schematic isometric view of an alternate embodiment of the sensor array in the system of FIG. 1.

FIGS. 6 and 7 are schematic isometric views of sensor arrays 34 positionable exterior of the body (FIG. 6) and spaced apart from the markers 30 positioned in or near the target 12. In these illustrated embodiments, three markers 30 are shown implanted in or near the target 12. As seen in FIG. 6, the sensor array 34 includes a frame 70 that supports a plurality of sensors 36 in a fixed and known geometry relative to each other along X, Y, or Z axes of a reference coordinate system 72. The position of each sensor 36 on the frame 70 relative to the reference coordinate system 72 is fixed and defines fixed reference points for obtaining measurement data used by the computer controller 38. In the embodiment of FIG. 6, the frame 70 supports the sensors 36 so the sensors are positioned in a single plane. In the embodiment of FIG. 7, the frame 70 is shaped to support the sensors 36 in two orthogonal planes, so the sensors 36 are oriented along the X, Y, and Z axes of the reference coordinate system 72. Accordingly, the sensor array 34 provides the fixed reference structure from which measurements are taken and calculations performed to determine the relative positions of the target 12, the target isocenter 40 and the machine isocenter 22.

The illustrated embodiments of FIGS. 6 and 7 utilize "wireless" markers 30, so frequency multiplexing is utilized to distinguish the signals from the different markers. Each sensor 36 is a three-axis sensor that measures the absolute marker signal strengths from a respective one of the markers 30 relative to the X, Y, and Z axes. The absolute signal strength of the marker signal along each axis in the reference coordinate system 72 is measured by the sensors 36 for each marker in order to determine the X, Y, and Z position of each marker.

It is known that the strength of a magnetic field decreases at a ratio proportional to the cube of the distance from the source. Accordingly, the distance of the marker from the sensor can be determined based upon the marker's signal strength. The geometric relationship from the marker to a series of sensors that are spaced at known locations relative to each other is used to solve a series of equations with one unique result. Accordingly, the distance between the marker 30 and the sensor 36 calculated by the computer controller 38 based on the marker's signal strength measured by the respective sensors and iterated for a best fit solution to the geometric equations.

Figure 8:
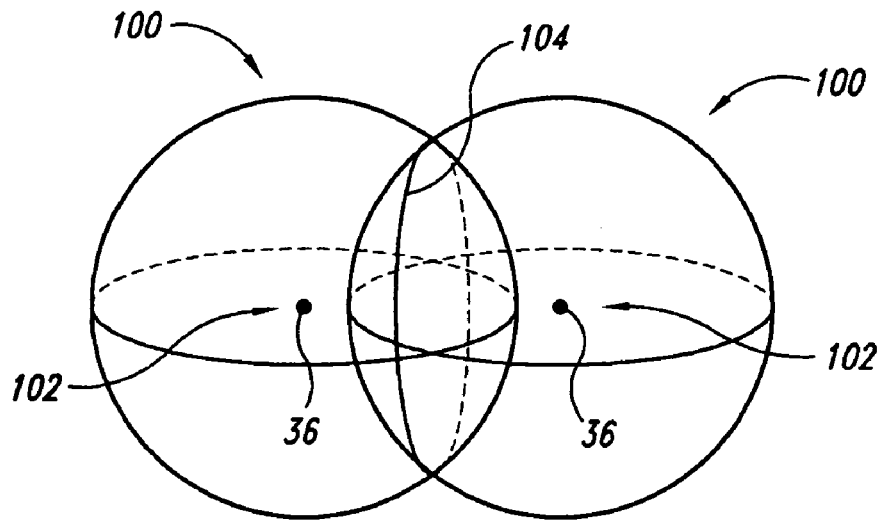
FIG. 8 is a geometric representation of two intersecting spheres representing data for determining a marker's position relative to two sensors.
Figure 9:
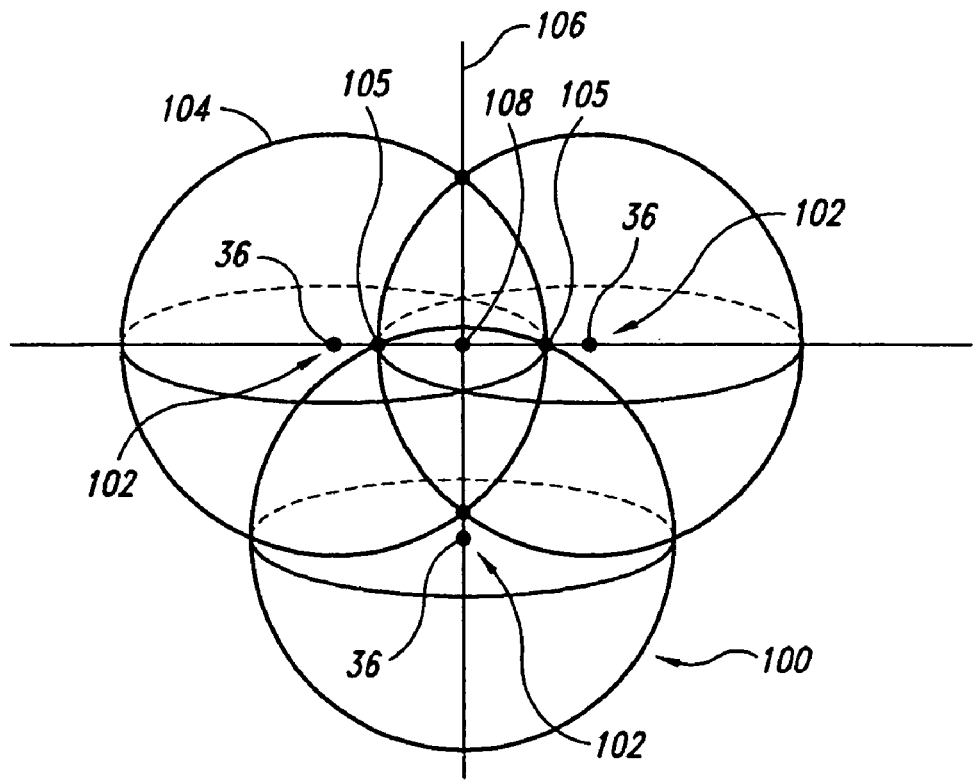
FIG. 9 is a geometric representation of four intersecting spheres representing data for determining a marker's position relative to four sensors.

The precise location of a marker 30 in space relative to the sensor array 34 can be calculated based upon the distances between that marker and at least four separate three-axis sensors spaced apart from each other in the array. The absolute magnitude of the distance from the three-axis sensor is determined by squaring the each of the three axis magnitudes (x, y, and z orientations), adding the results and finally taking the square root for the distance resultant. As an example, the distance between one sensor 36 and one of the markers 30 corresponds geometrically to the radius of a sphere. FIG. 8 shows two illustrative spheres 100 with the center points 102 each defined by a separate sensor 36. When two spheres 100 intersect, the intersection defines a circle 104. So, it is known that the marker is located at some point on that circle. When three spheres 100 intersect, shown in FIG. 9, the intersection defines one of two points 105 where the marker is located on that line. When four spheres 100 intersect, the intersection defines a single point 108 in space corresponding to the precise position of the marker 30 in space relative to the sensor array 34.

In an embodiment using a single marker 30 implanted in a target 12, the sensor array 34 can include only four three-axis sensors 36 to determine that marker's position in space. Since the signals are frequency multiplexed and multiple frequencies may be received with each sensor coil and each individual frequency component may be examined by processing the combined signal with a fast Fourier transform (FFT) in the control electronics, multiple markers may be located with the same sensors. In the embodiments with three or more markers 30 positioned in or near the target 12, the sensor array 34 is configured at known geometric orientations relative to the reference coordinate system 72, so that the marker signal measurements can be used by the computer controller 38 to calculate the angular orientation of the treatment volume (i.e., the pitch, yaw and roll) in space relative to the reference coordinate system 72 by using the three sets of three dimensional data (x, y, and z from the single axis markers). Based upon the position of the markers 30 relative to the target, the location and angular orientation of the target 12 can be determined by the computer controller 38.

The marker signal may be separated from the signal generated by the excitation source 32 via signal processing software or electronics in a number of ways. In one embodiment, the excitation source 32 is turned or gated "on" to excite the marker and then turned or gated "off" to allow for measurement of the marker response without interference by the signal from the excitation source. The marker 30 will continue to resonate after the excitation source 32 is gated "off" for a period determined by the sensor's electric inductance, capacitance and series resistance. In another embodiment, the system is operated in continuous wave (CW) mode where the excitation source 32 remains "on" during measurement of the markers 30. The marker signal is 90 degrees "out of phase" with the signal from the excitation source, so the marker signal is removed from the excitation signal. The time of the zero crossing of the excitation signal is known and the remaining marker signal will be at its peak intensity at that time. In a third embodiment, the output frequency of the excitation source's signal is continuously varied or scanned to maximize the excitation of the markers 30 which results in a maximum marker signal while minimizing or eliminating unwanted excitation signal.

The position of each marker 30 relative to the target 12 and relative to the target isocenter 40 is also calculated or determined. In one embodiment, the target isocenter 40 in the target 12 is chosen first based upon imaging data about the target provided by an imaging system, such as a CT scan, MRI, ultrasound system, or nuclear imaging system (e.g. positron emission tomography). Once the target isocenter 40 is selected, the position of each implanted marker 30 is measured relative to the target isocenter 40. The position of the target isocenter 40 is then determined relative to the reference coordinate system 72 based upon defining the location of each marker 12 relative to the reference coordinate system.

In another embodiment, the target isocenter 40 is defined as a function of the marker locations relative to the target 12. The markers 30 are selectively positioned in or near the target 12 and the orientation of the markers is used to define and calculate the target isocenter. Thus, the target isocenter 40 within the target 12 can be defined and its position determined relative to markers 30 and the reference coordinate system 72 even if the markers 30 are not actually implanted within or even immediately adjacent to the target 12. The markers 30 are, however, positioned close enough to the target 12 so that if the target moves, the target and markers move together substantially as a unit. Therefore, movement of the target 12 is monitored by tracking movement of the markers 30 relative to the sensor array 34.

The system 10 is configured to track motion of the target 12 in real time. When the portion of the patient's body 14 containing the target 12 and markers 30 is positioned adjacent to the sensor array 34 and the markers are energized, the computer controller 38 acquires data from each sensor 36 and outputs a result approximately 12 times per second. The computer controller obtains measurement data from the sensors 36 and calculates the location of the target isocenter 40 relative to the sensor array every five seconds. In alternate embodiments, the computer controller 38 can measure the sensors 36 to monitor in real time the motion of the particular target isocenter 40 relative to the sensor array 34. The measurement update rate may be reduce as to allow for sufficient data averaging to reduce the measurement noise at the same time allowing for an adequate update rate for the user.

Figure 10:
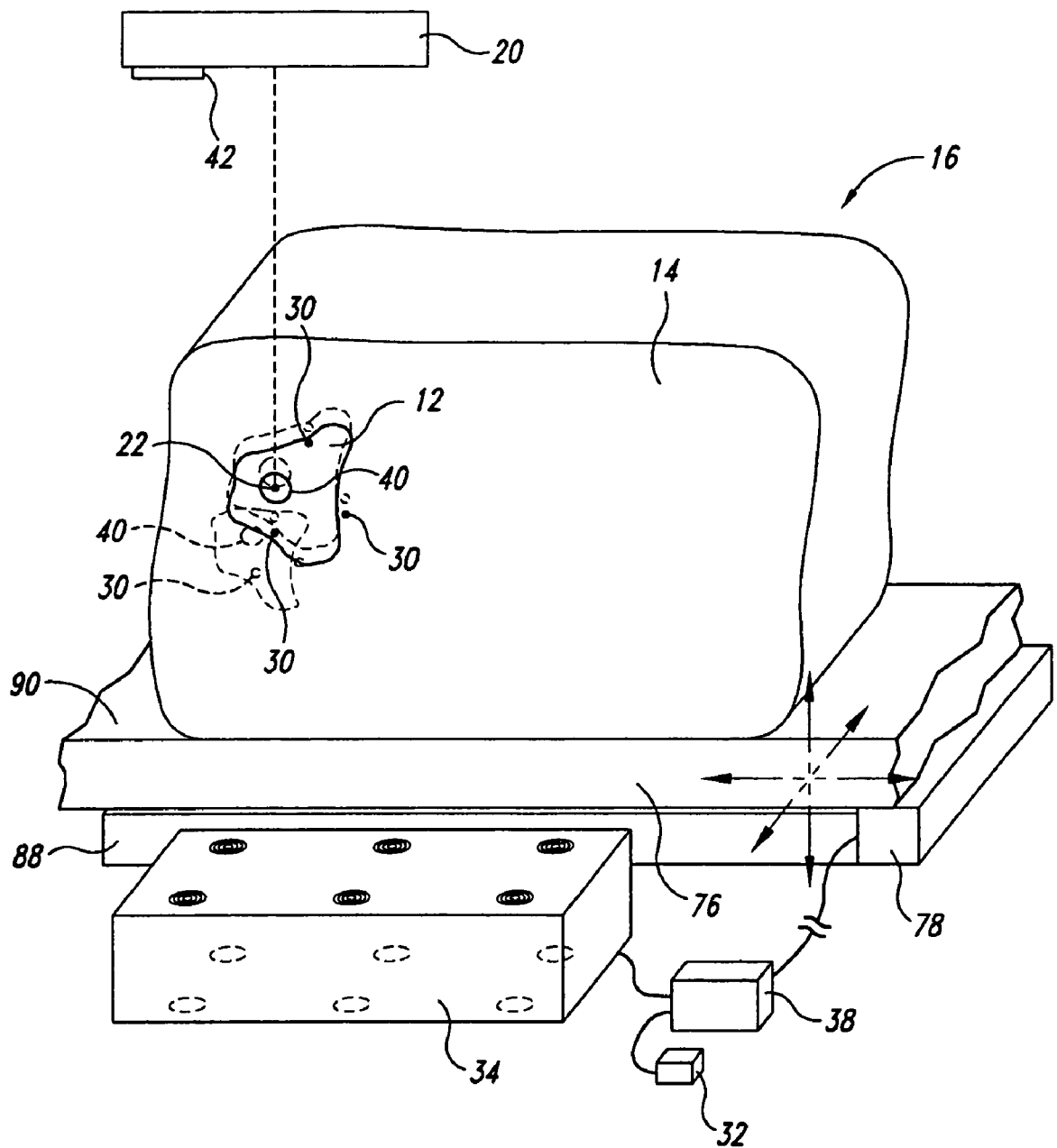
FIG. 10 is a schematic isometric view of a target in a body shown in phantom lines in a first position and shown in solid lines in a second, different position within the body.

FIG. 10 is a partial isometric view illustrating an aspect of the present invention that includes a support table 76 that movably supports the patient's body 14 under the gantry 20 and adjacent to the sensor array 34. The support table 76 is positionable below the machine isocenter 22. The support table 76 is movable to adjust the position of the patient 16 relative to the machine isocenter 22 until the target isocenter 40 is coincident with the machine isocenter. The sensor array 34 may be placed on, under, or connected to the support table 76. Alternatively, it may be mounted to the linear accelerator's gantry at a location sufficiently close to any markers 30 (implanted, external or gantry) that are to be located. In this alternate embodiment with the sensor array 34 mounted to the linear accelerator, the position from the machine isocenter 22 to the sensor array will be known, so that a separate gantry marker 42 may not be used.

As best seen in FIGS. 1 and 10, the support table 76 has a base 88 and a tabletop 90 movably supported to the base for linear and angular movement relative to the sensor array 34. A movement control system 78 is connected to the tabletop 90 to control movement of the tabletop and the patient 16 relative to the machine isocenter 22 and the sensor array 34. The control system 78 is also coupled to the computer controller 38, and the computer controller 38 is programmed to activate the control system 78 to adjust the linear or angular position of the patient. In one embodiment, the tabletop's position moves in response to an authorized user such as doctor, physicist or technician activating the control system, or automatically in response to instructions provided by the computer controller 38.

Once the target 12 is positioned so the target isocenter 40 is coincident with the machine isocenter 22, ionizing radiation can be selectively and very accurately delivered directly to the target area or volume. Application of the radiation therapy to the target 12, can be provided at the selected dosage and intensity with precise accuracy, while potentially minimizing the margin needed around the target. In one embodiment, the actual position of the target isocenter 40 is substantially continuously monitored and tracked relative to the machine isocenter 22 during delivery of the radiation therapy. If the target isocenter 40 moves away from the machine isocenter 22 beyond an acceptable range of displacement distances, the computer controller 38 provides a signal to the radiation delivery device to interrupt the radiation therapy to the target. The target's position can then be adjusted manually or automatically until the target isocenter 40 is again coincident with the machine isocenter 22, and radiation therapy can resume. In one embodiment, the computer controller 38 is programmed so that if the target isocenter 40 moves from the machine isocenter 22, but the distance of movement does not exceed the acceptable range, the computer controller 38 will not interrupt the radiation therapy. This range of movement is dependent upon many factors, such as the target type (e.g., prostate, lung, liver), target size, target location, beam shape/size, and the radiation treatment plan.

Figure 11:
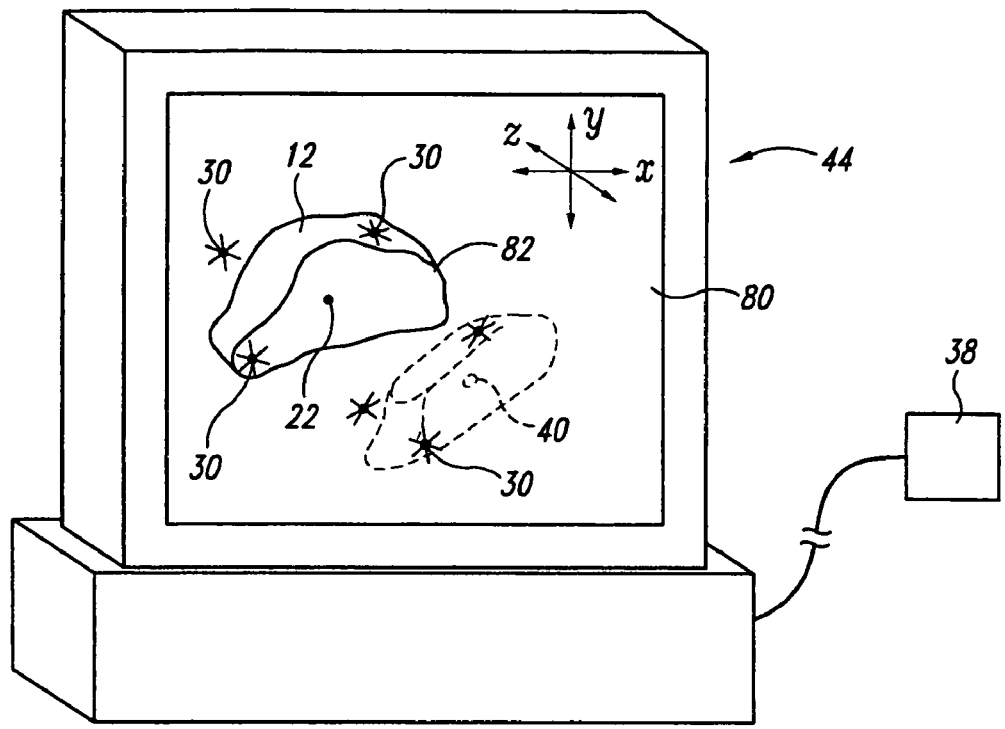
FIG. 11 is an enlarged isometric view of the monitoring system of FIG. 1 showing a simulated target, simulated markers, and a simulated target isocenter shown in phantom lines on a display screen, and actual marker locations and target isocenter locations shown in solid lines on the display screen.
Figure 12:
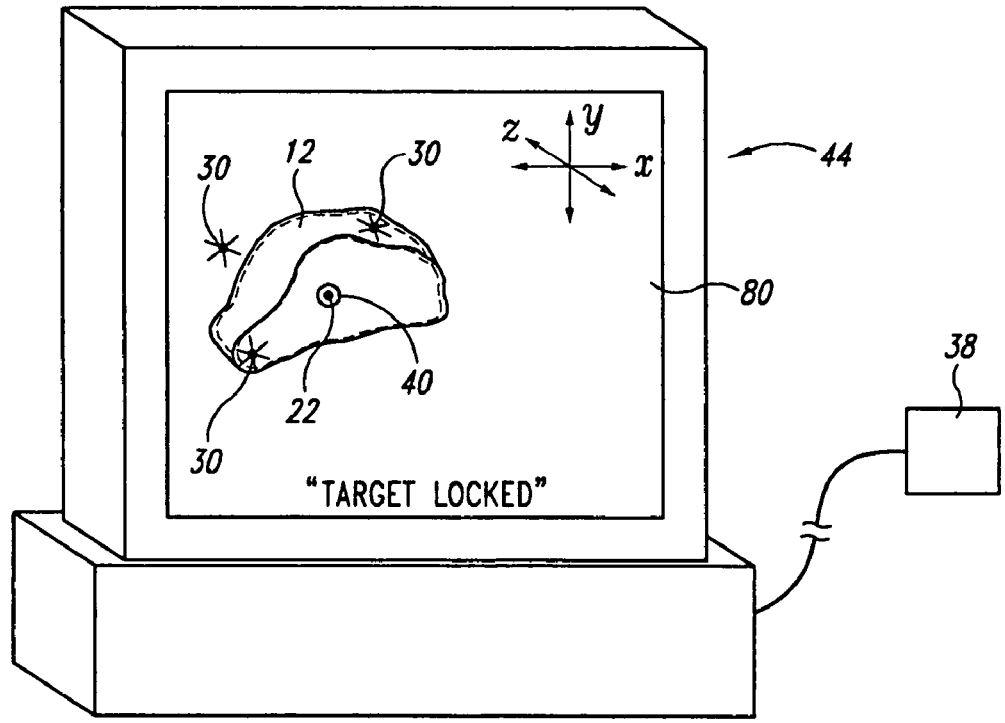
FIG. 12 is an isometric view of the monitoring system of FIG. 11 with the simulated and actual markers shown aligned with each other, and the machine isocenter and target isocenter coincident with each other.

Tracking of the target isocenter's position is facilitated by the monitoring assembly 44, which is coupled to the computer controller 38. FIGS. 11 and 12 illustrate a feedback portion 80 of the monitoring assembly 44 that provides feedback data to an operator about, as an example, the position of the markers 30, the target isocenter 40 and the machine isocenter 22. The feedback portion 80 is a display monitor that provides pictorial, graphical, or textual information to the operator. Other feedback portions 80, such as graphical display devices, auditory feedback devices, or visual feedback devices can be used in alternate embodiments. In one embodiment, the computer controller 38 contains imaging data, such as from a CT, MRI, or ultrasound imaging system, that defines the shape and size of the target 12 within the body 14. The imaging data also defines the locations of each marker 30 in or around the target 12. The computer controller 38 uses the imaging data to provide a simulated model of the target, the markers, and the target isocenter. This simulated model is displayed on the feedback portion 80 as shown in FIG. 11 in phantom lines. The simulated model is also displayed overlaying the machine isocenter 22, so the simulated target isocenter 40 is coincident with the machine isocenter. The simulated target and simulated markers can also display how the actual target needs to be positioned and oriented three-dimensionally for the particular radiation therapy to be applied to the target.

The monitoring assembly 44 also receives and displays information from the computer controller 38 to show the actual locations of the markers 30 and target isocenter 40 relative to the machine isocenter 22, and relative to the simulated target and markers. Accordingly, the feedback portion 80 allows the operator to determine the actual position of the markers relative to the simulated markers, and the target isocenter 40 relative to the machine isocenter 22 substantially in real time while the patient 16 is on the support table 76 (FIG. 1). The patient 16 and support table 76 can be repositioned until the target 12 is properly oriented for the selected radiation therapy.

Figure 13:
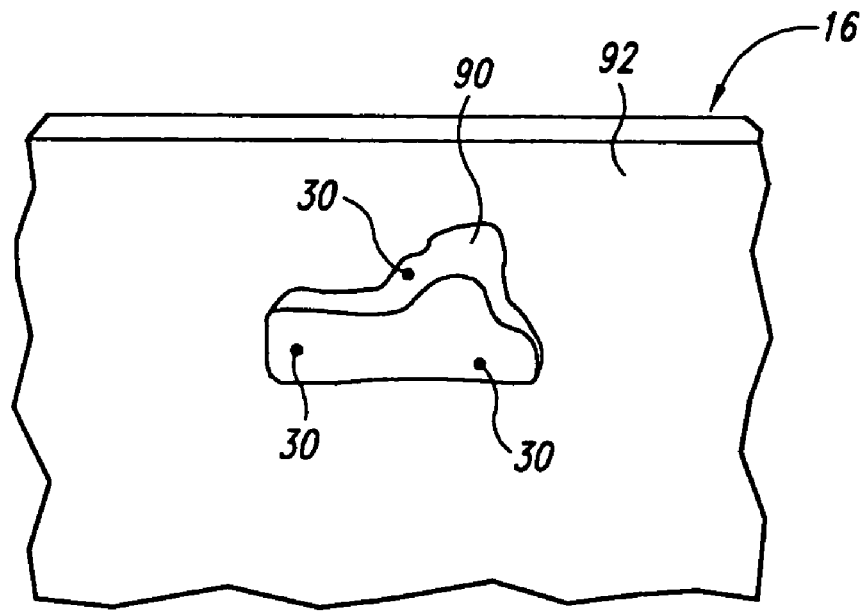
FIG. 13 is a simulated isometric view of a target and markers illustrated on the monitoring system, and the target is shown in a first target condition.
Figure 14:
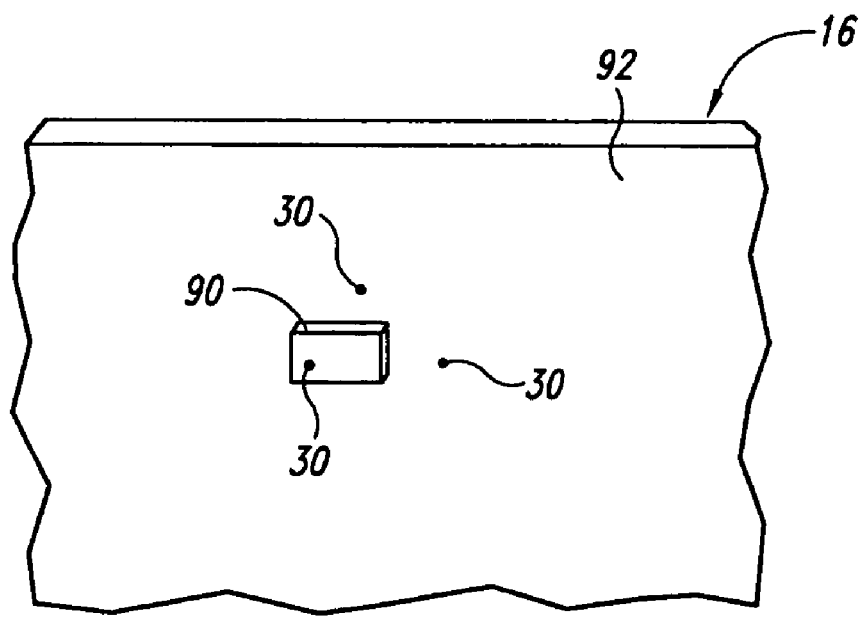
FIG. 14 is a simulated isometric view of the target and markers of FIG. 13, and the target is shown in a second condition representing a change in the target size or condition relative to the markers.
Figure 15:
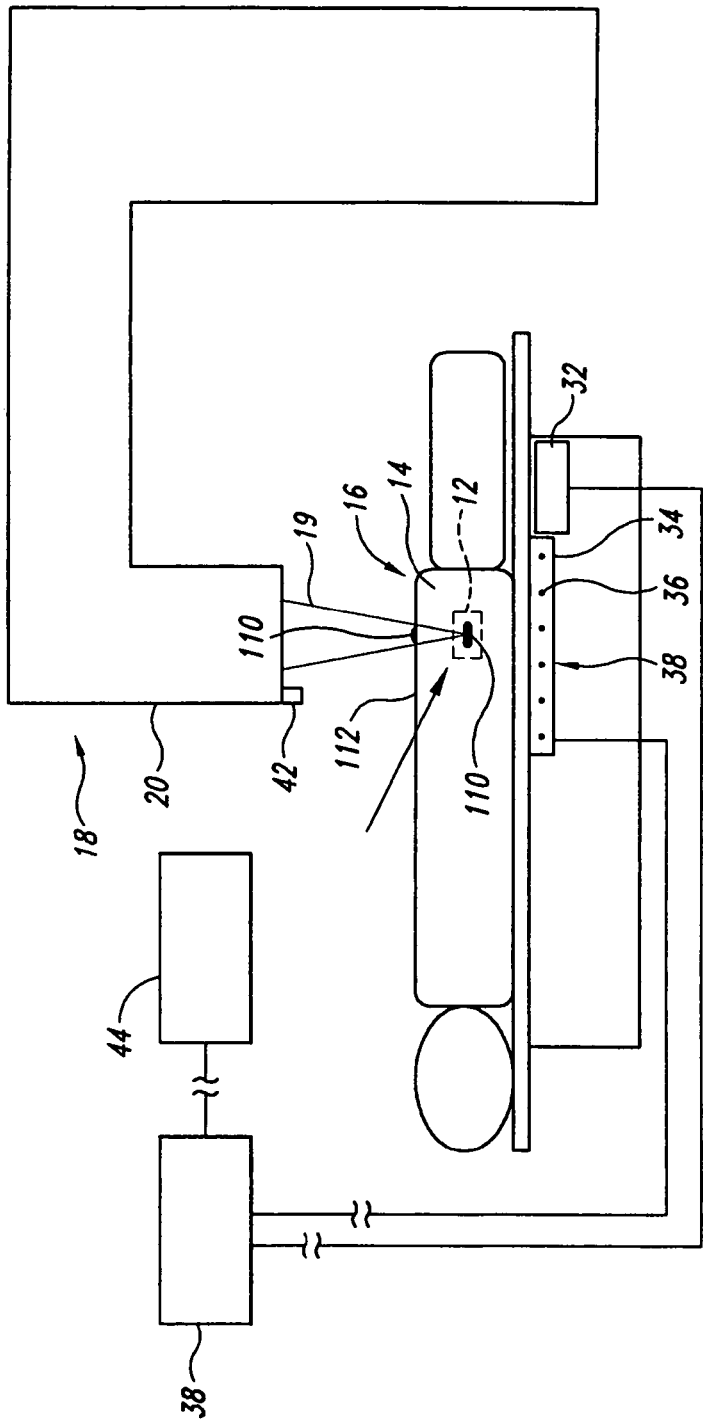
FIG. 15 is a side elevation view of an alternate embodiment of the present invention with surface markers mounted to an external surface of the patient's body and in alignment with each other and the target.
Figure 16:
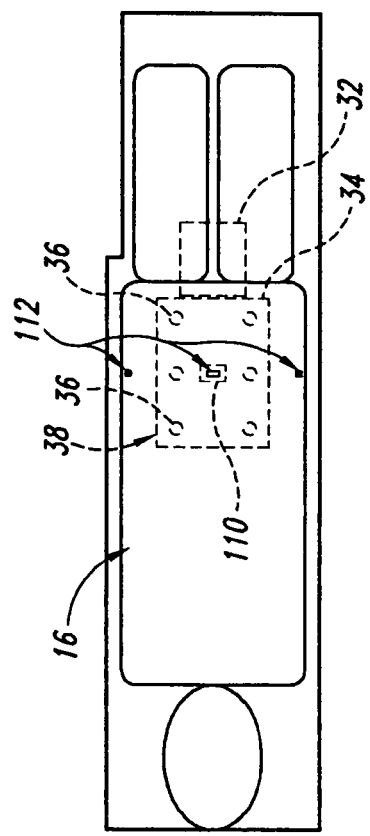
FIG. 16 is a top plan view of all of the patient with the surface-mounted markers of FIG. 15 mounted thereon.
Figure 17:
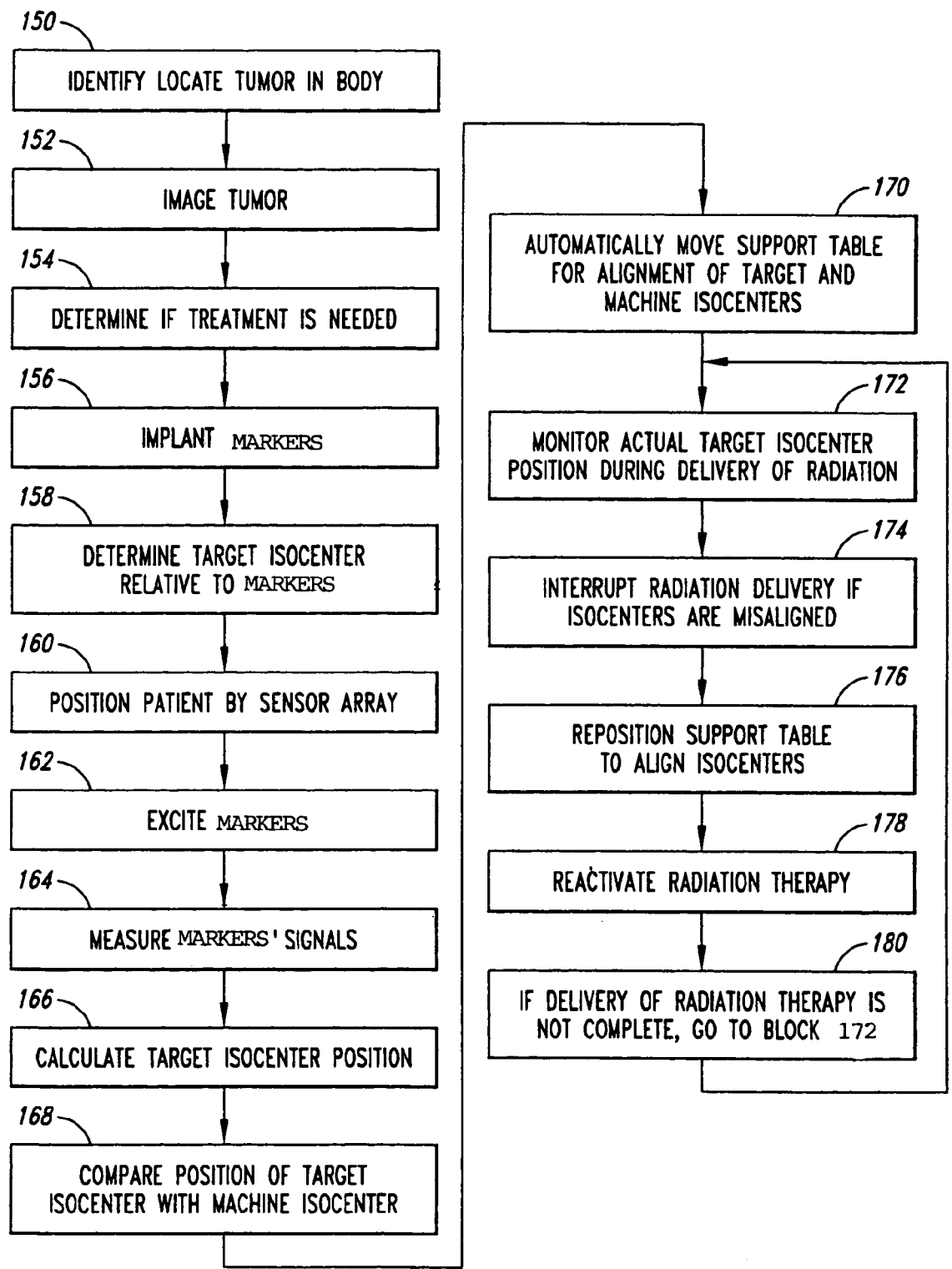
FIG. 17 is a schematic flow diagram of a radiation delivery process for delivering radiation treatment to a target utilizing the system of FIG. 1.

In addition to accurately tracking and monitoring the position of the target 12 relative to the machine isocenter 22, the system 10 is also usable to monitor the status of the target, such as a tumor or the like, in a patient's body 14 over time. FIGS. 13 and 14 are schematic views showing a tumor 90 in a body 92. Three markers 30 are shown for this embodiment permanently implanted in or adjacent to the tumor 90. Images of the tumor 90 and markers 30 are obtained by CT, MRI, ultrasound, or other imaging technique over time. From these multiple images of the tumor 90 and markers 30, the position of the markers relative to the tumor can be compared and tracked. Accordingly, a doctor can use the markers 30 in the multiple images as a reference tool to determine whether the tumor has shrunk, grown, moved, or otherwise changed within the patient's body.

As an example, FIG. 13 illustrates an image of a tumor 90 in a first condition with three markers 30 implanted therein, and FIG. 14 illustrates a second image of the tumor taken later in time. The second image shows the same markers 30 in the same location within the patient's body, and from the position of the tumor relative to the markers, one can see that the tumor has shrunk. Thus, doctors can track the status of tumors or other targets within the body over time to determine, as an example, the effectiveness of radiation therapy, whether additional treatments are needed, or whether a change in tumor growth has occurred or whether the radiation treatment plan needs to be altered.

In the embodiments discussed above, the markers 30 are described and shown as being subcutaneously implanted in or next to a target 12. This implantation of the markers 30 is performed when needed to ensure that, if the target 12 moves, the markers will move with the target as a unit. In an alternate embodiment illustrated in FIGS. 15 and 16, the markers are surface-mounted markers 110 adhered to the exterior surface 112 of the patient's body 14 substantially adjacent to and in alignment with a target 12, in or on the body. The surface-mounted markers 110 can be removably adhered with an adhesive, such as tape or the like, in a substantially fixed location on the body's exterior surface 112 relative to the target 12. These surface-mounted markers 110 are particularly suitable for targets 12 known not to substantially move within the body 14 relative to the exterior surface. The surface-mounted markers 30 are also suitable for use when the target's size or location in the body 14 is such that some motion of the target isocenter is not critical for effective radiation therapy or treatment. Accordingly, the surface-mounted markers 110 provide reference points for accurate alignment and orientation of the target 12 and the machine isocenter 22. Alternatively, markers 30 may be mounted on or in patient immobilization devices at known locations relative to the treatment isocenter.

The surface-mounted markers 110 in one embodiment are wireless markers, so that the markers can remain adhered on the patient's body 14 after a radiation treatment session so that the patient 16 can come and go from the treatment area without disrupting the position of the markers 110 relative to the target 12. In alternate embodiments, the markers 110 remain adhered to the patient 16 and are connectable to lead wires of a "wired" marker system in the treatment area. The lead wires can be disconnected from the markers 110 to allow the patient 16, to leave the treatment area while the markers remain fixed in place on the patient's body.

The surface-mounted markers 110 are also usable to monitor a patient's base-line girth (anterior-posterior and lateral dimensions) during a radiation treatment program. The base-line girth measurements, referred to as patient separations, are initially obtained by CT, MRI, or physical measurements. Patient separations are used when preparing a radiation treatment plan for the patient. The surface-mounted markers 100 can be utilized alone or in combination with implanted markers to provide data about changes in the patient separations that may occur during chemo radiotherapy. Each surface-mounted marker 110 has an identifiable initial position in space relative to, as an example, the target isocenter or relative to each other. The sensor array 34 and computer controller 38 are configured to determine the distances between each surface-mounted marker and/or the target isocenter. The computer controller 38 calculates and monitors the distances, corresponding to the patient separations. During the course of radiation treatment, if the patient separations change significantly, such as due to substantial weight loss from chemo or radiotherapy, the treatment plan may become invalid because less patient tissue is available to alternate the radiation beam, thereby resulting in higher than planned doses of radiation.

In one embodiment, the surface-mounted markers 110 are usable to facilitate and speed up patient set-up procedures before and/or during the radiation therapy procedure. The surface mounted markers 110 are positioned at selected locations on the patient's body 14 at known positions. The markers 110 are excited and the locations relative to the sensor array are determined. The marker's location information can then be used to calculate the Target Skin Distance or Source Skin Distance, which is the distance between the exterior skin of the patient and the linear actuator or the tabletop. The markers 110 can also be used to determine the tabletop-to-isocenter, which is the distance between the tabletop to the marker or other alignment means, such as laser cross-hairs projected on to the patient's skin. Accordingly, the surface mounted markers 110 can be used to automatically calculate the relevant distances during the set up procedure to quickly determine if the patient is properly positioned in accordance with the radiation therapy treatment plan.

In another embodiment, the surface-mounted markers 110 can be used in conjunction with one or more markers 30 implanted in or near the target 12. The relative location of each marker 110 or 30 can be calculated and used for any combination of patient set-up, target locating, target positioning, target motion tracking, and/or target evaluation, as discussed above.

The system 10 is also adapted for use in an automated patient setup process prior to delivery of the radiation therapy. The automated setup process of one embodiment is shown schematically as a flow chart in FIG. 17. In this patient setup process, the tumor or other target in the patient's body is identified (reference block 150). Images of the target are obtained (reference block 152), such as by X-rays, CT, MRI, nuclear imaging, or ultrasound imaging. The doctor and/or technicians then determine a treatment plan for the particular tumor (reference block 154). One or more markers are implanted in or on the body in selected positions relative to the target (reference block 156), and the location of the treatment isocenter relative to the markers is determined or calculated (reference block 158).

The patient is positioned on the movable support table so the target and markers are generally adjacent to the sensor array (reference block 160). The excitation source is activated to energize the markers (reference block 162), and the sensors measure the strength of the signals from the markers (reference block 164). The computer controller calculates location of the markers and the target isocenter relative to the sensor array and the machine isocenter (reference block 166). The computer compares the position of the target isocenter and machine isocenter (reference block 168), and if the two isocenters are misaligned, the computer automatically activates the control system of the support table to move the tabletop relative to the machine isocenter until the target isocenter is coincident with the machine isocenter (reference block 170).

In one embodiment, the computer controller also determines the position and orientation of the markers relative to the position and orientation of simulated markers. If the markers are not properly aligned and oriented with the simulated markers, the support table is adjusted linearly and angularly as needed for proper marker alignment. This marker alignment properly positions the target volume along 6 dimensions, namely X, Y, Z, pitch, yaw, and roll. Accordingly, the patient is automatically positioned in the correct position relative to the machine isocenter for precise delivery of radiation therapy to the target.

In one embodiment of this automated setup process, the computer restricts the radiation delivery device from delivering the radiation beam until the target isocenter is coincident with the machine isocenter. The computer monitors the position of the target isocenter during delivery of the radiation treatment (reference block 172). If the target isocenter's position is outside a permitted degree or range of dislocation, the computer interrupts the delivery of the radiation isocenter (reference block 174). The computer can then automatically reposition the tabletop and the patient (as a unit) so the target is properly positioned with the target isocenter and is coincident with the machine isocenter (reference block 176), and the radiation therapy can be reactivated for continued irradiation of the target (reference block 178). If the delivery of the radiation therapy is not yet completed (reference block 180), the process returns to reference block 172 to monitor the target's position relative to the machine isocenter as the radiation is being delivered. Accordingly, adjustments can be made automatically to ensure that the radiation is accurately delivered to the target without requiring a large margin around the target.

Although specific embodiments of, and examples for, the present invention are described herein for illustrative purposes, various equivalent modifications can be made without departing from the spirit and scope of the invention, as will be recognized by those skilled in the relevant art. The teachings provided herein of the aspects of the present invention can be applied to locating, monitoring, and treating a target within a body, and not necessarily limited to the illustrative radiation treatment of the tumor in the body as described above.

In general, in the following claims, the terms used should not be construed to limit the invention to the specific embodiments disclosed in the specification and the claims, but should be construed to include all target locating and monitoring systems that operate in accordance with the claims to provide apparatus and methods for locating, monitoring, and/or tracking the position of a selected target within a body. Accordingly, the invention is not limited, except as by the appended claims.

The invention claimed is:

1. A control system for use in connection with a radiation delivery system having a radiation source that produces a radiation beam, a patient support, and a drive system that moves the patient support, the control system comprising:
 a wireless marker configured to be implanted in the patient at a site relative to a treatment target wherein the marker is energized or excited by an excitation source positioned exterior of the patient;
 sensors that obtains position information about the location and/or orientation of the marker; and
 a computer operatively coupled to the sensor, the computer having a computer operable medium containing instructions that cause the computer to (a) receive the position information from the sensors, (b) determine an actual location of the treatment target, (c) compute a displacement between the treatment target and a beam isocenter of the radiation beam, and (d) automatically control the radiation beam and/or move the patient support based on the computed displacement between the treatment target and the beam isocenter.

2. The control system of claim 1 wherein the instructions contained by the computer operable medium further cause the computer to compute the displacement between the treatment target and the beam isocenter in three dimensions based on the actual location of the treatment target at least every at least twelve times per minute while the sensor obtains the position information.

3. The control system of claim 1 wherein the instructions contained by the computer operable medium further cause the computer to operate the drive system to move the table so that the treatment target remains in an acceptable range of the beam isocenter.

4. The system of claim 1 wherein the instructions contained by the computer operable medium further cause the computer to operate the radiation source to interrupt the radiation beam when the computed displacement is not within an acceptable range.

5. A control system for use in connection with a radiation delivery system having a radiation source that produces a radiation beam, a patient support, and a drive system that moves the patient support, the control system comprising:
 a wireless marker configured to be implanted in the patient at a site relative to a treatment target wherein the marker is energized by an external excitation source;
 sensors that obtains position information about the location and/or orientation of the marker; and
 a computer operatively coupled to the sensor, the computer having a computer operable medium containing instructions that cause the computer to perform the method of (a) sensing the marker to obtain position information related to an actual position of the marker, (b) determining an actual location of the treatment target based on the sensed position information of the marker, and (c) controlling the radiation beam and/or movement of the patient automatically via a computer based on the actual position of the treatment target while sensing the marker.

6. A control system for use in connection with a radiation delivery system having a radiation source that produces a radiation beam, a patient support, and a drive system that moves the patient support, the control system comprising:
 a wireless marker configured to be implanted in the patient at a site relative to a treatment target wherein the marker is configured to provide a signal and is not physically connected with an outside energy source;
 sensors that obtains position information about the location and/or orientation of the marker; and
 a computer operatively coupled to the sensor, the computer having a computer operable medium containing instructions that cause the computer to perform the method of (a) sensing the marker to obtain position information related to an actual position of the marker, (b) determining an actual position of the treatment target based on the position information of the marker, (c) computing a displacement between the treatment target and a beam isocenter of the radiation beam in three dimensions based on the actual position of the treatment target, and (d) moving a patient support platform by automatic control when the displacement between the treatment target and the beam isocenter is beyond an acceptable range.

7. A control system for use in connection with a radiation delivery system having a radiation source that produces a radiation beam, a patient support, and a drive system that moves the patient support, the control system comprising:
 a wireless marker configured to be implanted in the patient at a site relative to a treatment target wherein the marker is energized or excited by an excitation source positioned exterior of the patent;
 sensors that obtains position information about the location and/or orientation of the marker; and
 a computer operatively coupled to the sensor, the computer having a computer operable medium containing instructions that cause the computer to perform a method while the patient is placed on the patient support such that the wireless marker can be sensed by the sensor, the method comprising (a) obtaining position information about the position and/or orientation of the wireless marker from the sensor, (b) determining an actual location of the treatment target based on the position information obtained from the sensor, (c) computing a displacement between the treatment target and a beam isocenter of the radiation beam, and (d) automatically moving the patient support and/or controlling the radiation beam via a computer based on the computed displacement between the treatment target and the beam isocenter.

8. A control system for use in connection with a radiation delivery system having a radiation source that produces a radiation beam, a patient support, and a drive system that moves the patient support, the control system comprising:

a wireless marker configured to be implanted in the patient at a site relative to a treatment target wherein the marker is configured to provide a signal and is not physically connected with an outside energy source;

sensors that obtains position information about the location and/or orientation of the marker; and a computer operatively coupled to the sensor, the computer having a computer operable medium containing instructions that cause the computer to perform a method while the patient is placed on the patient support such that the wireless marker can be sensed by the sensor, the method comprising (a) obtaining position information about the position and/or orientation of the wireless marker from the sensor, (b) determining an actual location of the treatment target based on the position information obtained from the sensor, (c) computing a displacement between the treatment target and a beam isocenter of the radiation beam, and (d) automatically moving the patient support and/or controlling the radiation beam via a computer based on the computed displacement between the treatment target and the beam isocenter.

9. A control system for use in connection with a radiation delivery system having a radiation source that produces a radiation beam, a patient support, and a drive system that moves the patient support, the control system comprising:

a wireless marker configured to be implanted in the patient at a site relative to a target in the patient wherein an excite source is configured to remain outside the patent and is configured to excite the marker;

sensors that obtains position information about the location and/or orientation of the marker; and a computer operatively coupled to the sensor, the computer having a computer operable medium containing instructions that cause the computer to perform the method of (a) sensing the marker to obtain position information related to an actual position of the marker, (b) determining an actual location of the target based on the sensed position information of the marker, and (c) controlling a radiation beam for treating the patient and/or movement of the patient automatically via a computer based on the actual position of the target while sensing the marker.

10. A control system for use in connection with a radiation delivery system having a radiation source that produces a radiation beam, a patient support, and a drive system that moves the patient support, the control system comprising:

a wireless marker configured to be implanted in the patient at a site relative to a Target wherein the marker is energized by an external energy source;

sensors that obtains position information about the location and/or orientation of the marker; and a computer operatively coupled to the sensor, the computer having a computer operable medium containing instructions that cause the computer to perform the method of (a) sensing the marker to obtain position information related to an actual position of the marker, (b) determining an actual location of the marker based on the sensed position information of the marker, and (c) controlling a radiation beam for treating the patient and/or movement of the patient automatically via a computer based on the actual position of the marker while sensing the marker.

* * * * *

UNITED STATES PATENT AND TRADEMARK OFFICE
CERTIFICATE OF CORRECTION

PATENT NO.       : 7,657,302 B2                                           Page 1 of 1
APPLICATION NO.  : 10/722015
DATED            : February 2, 2010
INVENTOR(S)      : Mate et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 752 days.

Signed and Sealed this

Thirtieth Day of November, 2010

David J. Kappos
*Director of the United States Patent and Trademark Office*